United States Patent
Fraser et al.

(10) Patent No.: US 7,278,325 B2
(45) Date of Patent: Oct. 9, 2007

(54) METHOD AND APPARATUS TO MEASURE FLOW RATE

(75) Inventors: Jamie Stuart Fraser, Repton (GB); Robert Richard Thurston, deceased, late of Melbourne (GB); by Loraine Thurston, legal representative, Melbourne (GB)

(73) Assignee: Lattice Intellectual Property, Ltd., London (GB)

( * ) Notice: Subject to any disclaimer, the term of this patent is extended or adjusted under 35 U.S.C. 154(b) by 101 days.

(21) Appl. No.: 10/257,953

(22) PCT Filed: Apr. 24, 2001

(86) PCT No.: PCT/GB01/01806

§ 371 (c)(1),
(2), (4) Date: Aug. 16, 2005

(87) PCT Pub. No.: WO01/81873

PCT Pub. Date: Nov. 1, 2001

(65) Prior Publication Data

US 2006/0010987 A1 Jan. 19, 2006

(30) Foreign Application Priority Data

Apr. 27, 2000 (GB) .................................. 00101584

(51) Int. Cl.
*G01F 1/704* (2006.01)
(52) U.S. Cl. .................................................. 73/861.07
(58) Field of Classification Search .............. 73/865.8, 73/61.62, 861.07, 861.05, 40.7
See application file for complete search history.

(56) References Cited

U.S. PATENT DOCUMENTS

| 3,435,660 A | 4/1969 | Stemberg |
| 3,722,276 A | 3/1973 | Chandler et al. |
| 3,881,351 A | 5/1975 | Prachar |
| 4,805,450 A | 2/1989 | Bennett et al. |
| 4,946,555 A | 8/1990 | Lee et al. |
| 5,567,885 A * | 10/1996 | Garside .................. 73/861.07 |
| 7,047,830 B2 * | 5/2006 | Bratton et al. ............. 73/865.8 |
| 7,051,578 B2 * | 5/2006 | McCoy et al. ............... 73/40.7 |
| 2005/0034533 A1 * | 2/2005 | Wang ...................... 73/861.05 |

FOREIGN PATENT DOCUMENTS

| DE | 20 44 407 | 3/1972 |
| EP | 0 400 707 | 12/1990 |
| EP | 0472131 | 8/1991 |
| EP | 0 855 578 | 7/1998 |

* cited by examiner

*Primary Examiner*—Jewel Thompson
(74) *Attorney, Agent, or Firm*—Oblon, Spivak, McClelland, Maier & Neustadt, P.C.

(57) ABSTRACT

A method and apparatus for measuring the flow rate of a single phase fluid, particularly a gas, through a conduit. A pulse of tracer fluid is discharged or injected into a first fluid flowing through a conduit, the concentration of the tracer fluid is measured as a function of time at a downstream from where it is injected, and the flow rate of the first fluid is determined based on the concentration measurements. The concentration of tracer fluid is preferably sampled substantially continuously from when the tracer gas first passes the measuring point until substantially all of the tracer fluid has passed the measuring point and the sampled concentrations integrated. The concentration of tracer fluid is preferably determined by measuring the thermal conductivity of the mixture of the first fluid and tracer fluid which is dependent upon the concentration of the tracer fluid.

40 Claims, 2 Drawing Sheets

METHOD AND APPARATUS TO MEASURE FLOW RATE

The present invention relates to a method and apparatus for measuring the rate of flow of a fluid, particularly a gas, through a conduit.

The flow rate of a fluid through a pipe can be measured using 'time of flight' methods in which a marker is introduced into the fluid flowing in the pipe and the time taken for the marker to travel a known distance along the pipe is measured. Such a method is disclosed in U.S. Pat. No. 5,646,354 in which microwave radiation is injected into a flowing stream of material to heat the material at that point. A temperature sensor is positioned a known distance from the point at which the flowing material is heated and the time taken by the heated material to reach the temperature sensor is measured.

However, a number of problems arise with 'time of flight' methods of measuring flow rate. For example, the volume between the point at which the marker is introduced and the point at which the marker is detected must be known precisely. This can be difficult to determine if the conduit through which the fluid flows is difficult to access, such as if it is underground. Furthermore, the conduit through which the marker travels should be straight as any bends would lead to uncertainty as to the actual distance travelled by the marker which could follow one of a number of paths around the bend. Thus such a 'time of flight' meter would be difficult to apply in many circumstances such as a local transmission network supplying gas to consumers as the pipes of such a network are generally concealed underground and have many bends.

It is an object of the present invention to be able to measure the flow rate of a fluid through a conduit whilst overcoming one or more of the problems previously mentioned. According to a first aspect of the present invention, a method of measuring the flow rate of a first substantially single phase fluid flowing through a conduit comprises:

discharging a known or determinable molar quantity of a tracer fluid into a first fluid flowing through a conduit;

measuring the concentration of the tracer fluid as a function of time at a suitable point downstream from where it is discharged, and determining the flow rate of the first fluid through the conduit dependent upon the molar quantity of a tracer fluid discharged and the measured concentration of the tracer fluid at the suitable point downstream.

Using this technique, the flow rate of a fluid may be determined independent of or without the need for details of the conduit geometry or a long straight length of conduit.

The concentration of the tracer fluid may be measured more than once or substantially continually monitored or sampled during the passage of the tracer fluid past the measuring point and the measured concentrations integrated or summed. The concentration of the tracer fluid is preferably measured from when the tracer fluid first passes the sampling point until all of the injected tracer fluid has passed. The flow rate of the first fluid is preferably determined dependent on the molar quantity of the injected tracer fluid as well as its measured concentration at a point downstream.

The first fluid and the tracer fluid are preferably single phase fluids, more preferably gases at ambient temperatures. The concentration of the tracer gas is preferably determined by measuring the thermal conductivity of the first fluid and tracer fluid mixture.

According to a second aspect of the present invention, an apparatus for measuring the flow rate of a first substantially single phase fluid through a conduit comprises:

a device for discharging a known or determinable molar quantity of tracer fluid into a first fluid flowing in a conduit;

means for measuring the concentration of the tracer fluid at a point downstream from where the discharging device is arranged to discharge the tracer fluid, and control means for determining the flow rate of a first fluid through a conduit dependent upon the concentration of the tracer fluid measured by the measuring means.

The means for measuring the concentration of the tracer fluid preferably comprises means for measuring the thermal conductivity of the mixture of first fluid and tracer fluid and means for converting the thermal conductivity measurement into a corresponding value indicative of the concentration of tracer fluid in the mixture.

The invention is described further by way of example with reference to the accompanying drawings, in which FIG. 1 diagrammatically shows an arrangement for measuring the flow rate of a fluid through a conduit;

Figure 1:
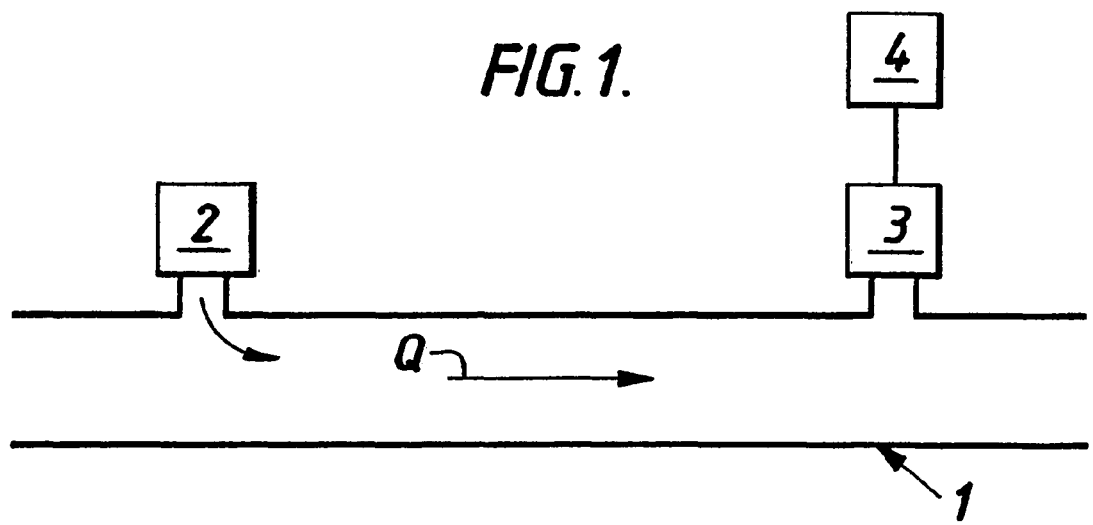

As shown in FIG. 1, a conduit for containing a fluid flowing therethrough with a flow rate Q is provided with a device 2 to discharge or inject a known or determinable molar quantity of tracer fluid into the conduit 1 and a detector 3, downstream of the injector 2, to measure the concentration of the tracer fluid as it passes. A control means 4 connected to the detector 3 is arranged to determine the flow rate Q of the fluid flowing through the conduit 1 based upon the molar quantity of tracer fluid injected and the concentration of the tracer fluid measured by the detector 3.

Figure 2:
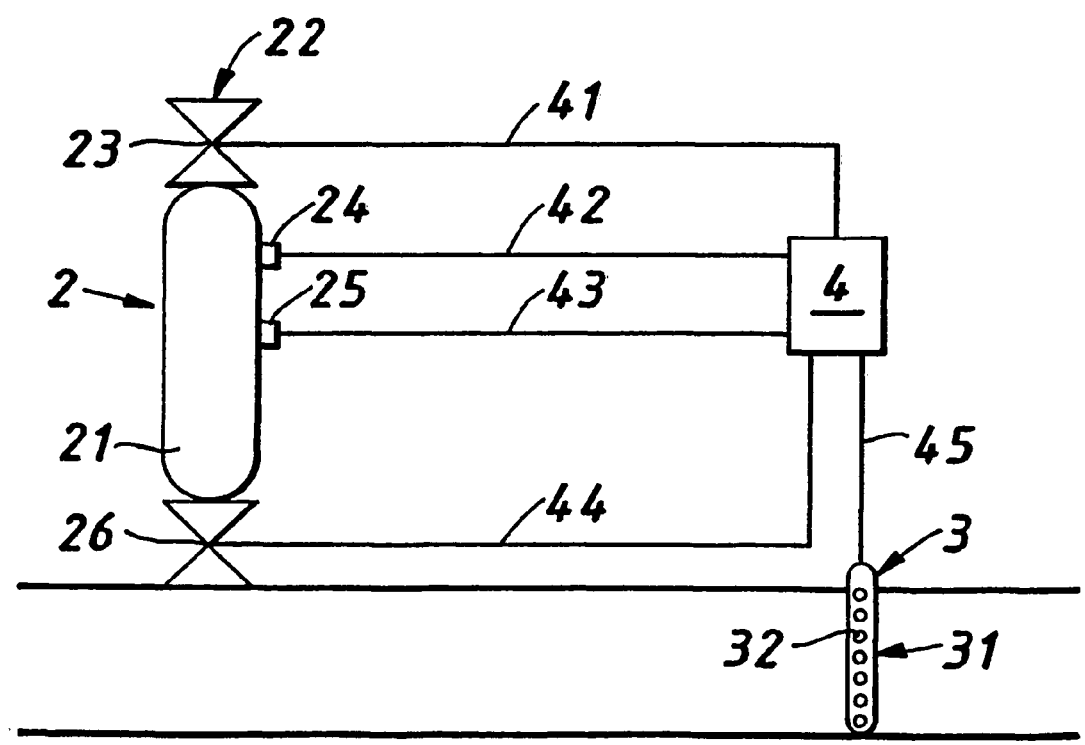
FIG. 2 shows the arrangement of FIG. 1 in more detail.

FIG. 2 shows the flow rate measuring apparatus of FIG. 1 in more detail. In this example the conduit 1 is a pipe arranged to convey fuel gas. However, the invention is applicable to the measurement of the flow rate of any fluid such as air or other gases. The injector 2 comprises a charge vessel 21 arranged to be charged with tracer fluid of a known concentration, in this case 100% helium, from a suitable source 22 such as a helium cylinder via a valve 23. Valve 23 is controlled by control means 4, which may be a portable computer or a processing means for example, via control line 41 to supply the charge vessel 21 with helium when required. The charge vessel 21 is provided with a pressure sensor 24 and a temperature sensor 25 to measure the pressure and temperature respectively of the tracer gas within the charge vessel 21. The control means 4 measures the pressure and temperature from sensors 24, 25 via lines 42 and 43 respectively. Using these sensors and knowing the volume of the charge vessel 21, the control means 4 is able to determine the molar quantity of helium in the charge vessel 21. The control means 4 can fill the charge vessel 21 with a desired quantity of helium by monitoring the pressure and temperature sensors 24, 25 and controlling valve 23. When it is desired to make a measurement of the flow rate Q of the fuel gas flowing through conduit 1, the control means 4 opens valve 26 via control line 44 for a quantity of tracer gas to pass into the conduit 1 to mix with the gas the flow rate of which is to be measured. The tracer gas is injected into conduit 1 through an injection unit to ensure good mixing with the fuel gas to obtain precise measurements with the detector 3. The molar quantity of tracer injected can then be determined by relating the initial and final pressures and temperatures, and the previously determined volume of the charge vessel 21.

The detector 3 may be any device capable of measuring the concentration of the passing tracer fluid. In this case the detector 3 measures the change in thermal conductivity of the passing mixture of fuel gas and tracer gas compared with the thermal conductivity of the fuel gas alone. Since thermal conductivity sensors such as those produced by Hartman & Braun of Germany are compact, reliable and inexpensive, their use in the present invention to determine the concentration of tracer gas produces a correspondingly compact, reliable and inexpensive flow rate measurement device. The thermal conductivity measured by sensor 3 is passed to control means 4 via line 45. Control means 4 determines a value corresponding to the concentration of tracer gas from the measured thermal conductivity. In this example, the control means 4 converts the measured thermal conductivity into a value corresponding to the concentration of tracer gas that would produce that change in the thermal conductivity measurement, using a predetermined concentration stored in correspondence to each of various possible measured changes in thermal conductivity. A table of measured changes in thermal conductivity with corresponding values of tracer gas concentration is prepared in advance by making measurements of the thermal conductivities of mixtures of a first fluid in this case natural gas, with various quantities of tracer fluid, in this case Helium. For even greater accuracy measurements of temperature and pressure may also be made at the point where the thermal conductivity is measured and look-up tables produced for each combination of temperature and pressure. Use of such a so-called look-up table considerably reduces the processing power required which reduces the cost and size of the device and increases its speed. Look-up tables of any suitable size may be used depending upon the precision required for the device. In another example the control means 4 is arranged to determine a value corresponding to the concentration of tracer gas from the thermal conductivity measurements of the detector 3 using suitable functions or algorithms. For even greater accuracy measurements may be made of the temperature and pressure at which the thermal conductivity is measured and these measurements taken into consideration by the suitable functions or algorithms which determine a value corresponding to the concentration of tracer gas at that temperature and pressure.

In this example, the conduit 1 is arranged to convey natural gas and the tracer gas is 100% helium. A measurement is also made of the thermal conductivity of the first fluid with no added tracer to provide an indication of the thermal conductivity of the natural gas which can vary with composition. The background thermal conductivity is then used as a baseline from which a change in thermal conductivity can be determined.

Figure 3:
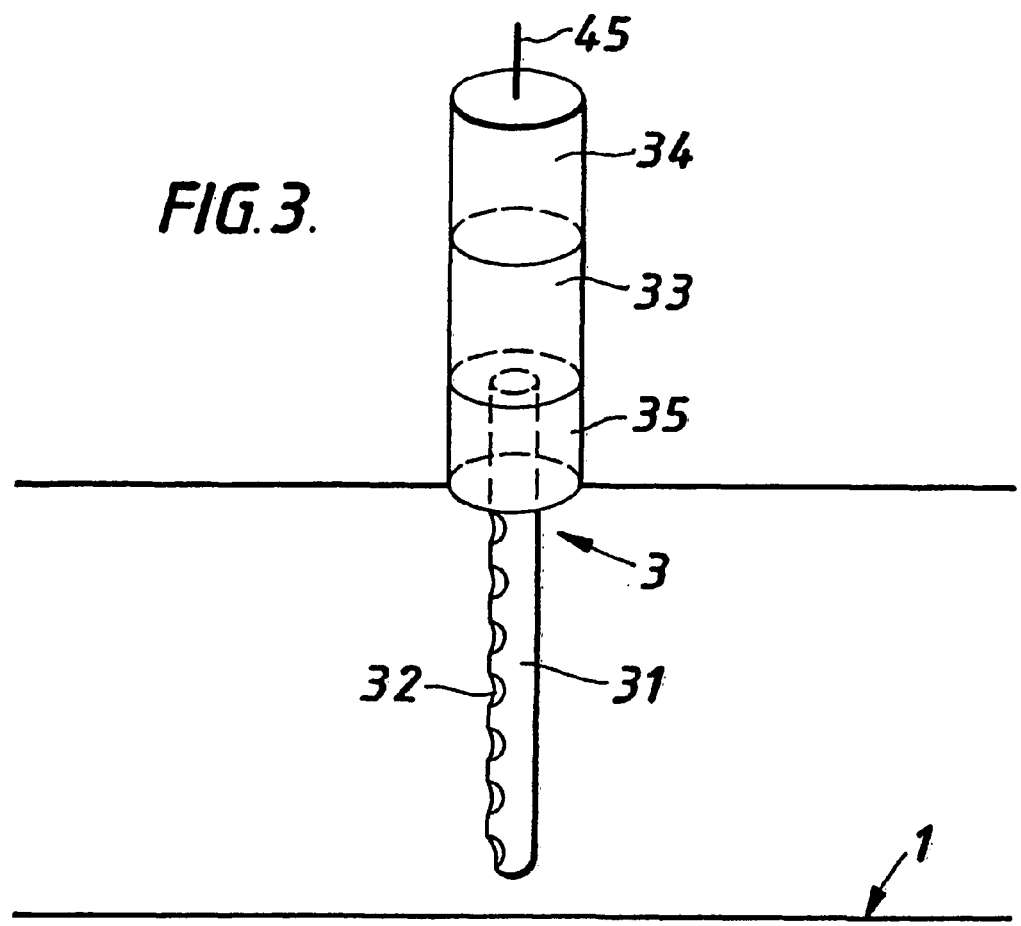
FIG. 3 shows a preferred form of fluid concentration detector.

The arrangement of the detector 3 used in this example is shown more clearly in FIG. 3. Gas from conduit 1 is sampled by a tube 31 arranged diametrically across the conduit 1 with a number of holes 32 arranged along the length of the tube 31 to receive gas flowing through the conduit 1. The sampled gas is conveyed up the tube 31 to a sampling chamber 33. The sampling chamber 33 presents the sampled gas to a thermal conductivity sensor 34 as is well known in the art which conveys an electrical signal indicative of the measured thermal conductivity to control means 4 via line 45. The sampled gas is returned to conduit 1 via return tube 35 which in this example surrounds tube 31. The continual flow of sampled fluid through the detector arrangement 3 enables a continual sampling of the concentration of the passing tracer gas to be made. Alternatively the thermal conductivity sensor 34 could be positioned in the conduit 1 directly in the gas flow such that the tubing arrangement is not required.

Figure 4:
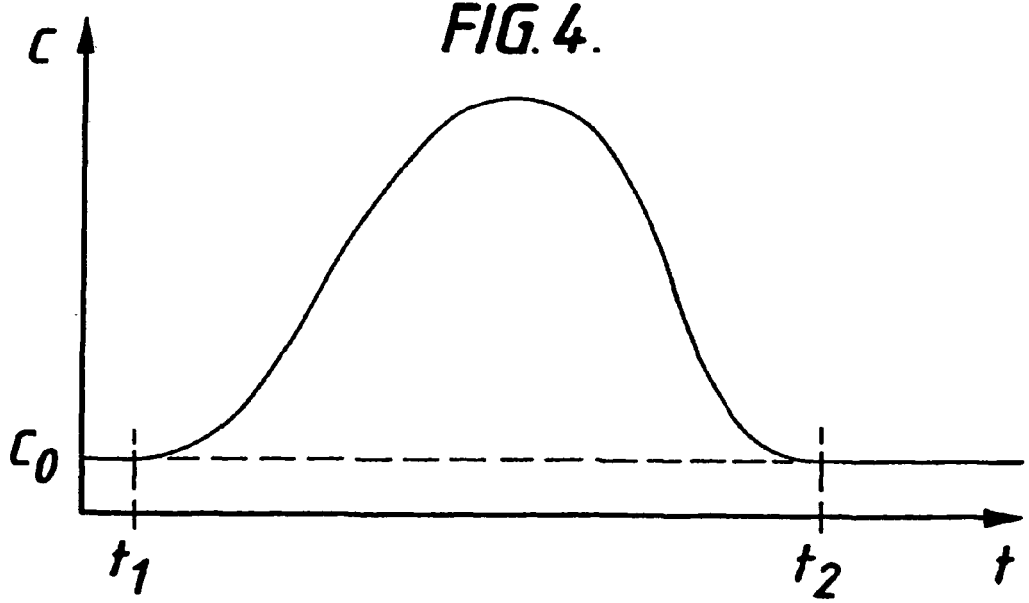
FIG. 4 shows a measured tracer concentration profile.

After the injector 2 has injected the tracer gas into the conduit 1, the control means 4 monitors the measurements of detector 3, which are indicative of the concentration of the passing tracer gas, for sufficient time to ensure that substantially all of the tracer gas has passed the sampling point. This results in a tracer concentration profile of the form shown in FIG. 4 with tracer concentration C plotted against time t. The tracer gas passes the detector between times $t_1$ and $t_2$ and a background level of tracer gas is indicated by $C_o$.

The control means 4 determines the actual flow rate Q of fluid through the conduit 1 dependent upon the measured concentration of tracer fluid C using the following function:

$$Q = \frac{VC_1}{\int_{t_1}^{t_2}(C-Co)dt}$$

Where V is the volume of the injected tracer fluid corrected to line conditions at the measuring point
$C_1$ is the concentration of the injected tracer fluid and
$C_o$ is the measured background level of tracer fluid (note: C is often taken as the increased concentration of tracer and Co is taken as zero) In practice, to integrate the measured concentration of tracer gas, measurements of concentration are sampled at regular intervals, in this case every millisecond, and the sampled measurements summed. Any suitable number and frequency of samples of the measured concentration may be taken depending upon the precision required.

Flow rate tests using the above apparatus with a measured concentration sampling period of every millisecond have produced flow rate results accurate to within 1%.

The volumetric flow rate Q determined by control means 4 may be displayed on a display means associated with the control means 4 or communicated to a suitable remote device.

The determined volumetric flow rates Q may be stored, preferably electronically, for subsequent analysis.

The flow meter described above is particularly suitable for use with subterranean local gas transmission pipes which deliver gas to consumers as the pipe geometry does not need to be known and a straight length of pipe is not required, and also to the in-situ testing of meters where components such as regulators make determining internal volumes difficult and where pipe lengths are short.

Many modifications may be made to the example described above without departing from the scope of the invention. For example, the invention may be used to determine the flow rate of any fluid such as natural gas or air. Furthermore any tracer fluid may be used provided its concentration may be measured and any technique for measuring the concentration of the tracer fluid may be used.

The invention claimed is:

1. A method of measuring a flow rate of a first single phase fluid flowing through a conduit, the method comprising:
   discharging a pulse of tracer fluid into a first fluid flowing through a conduit;
   determining a concentration of the tracer fluid at a suitable point downstream from the discharging; and determining a flow rate of the first fluid through the conduit dependent upon the molar quantity of the tracer fluid discharged and the measured concentration of the tracer fluid at the suitable point downstream, wherein the concentration of the tracer fluid is determined by measuring a change in thermal conductivity of a mixture of first fluid and tracer fluid compared with a thermal conductivity of the first fluid alone, which is a function of the concentration of the tracer fluid.

2. A method according to claim 1, wherein the concentration of the tracer fluid is determined from the measured thermal conductivity using a processing means using suitable algorithms.

3. A method according to claim 1, wherein the concentration of the tracer fluid is determined from the measured thermal conductivity using a look-up table.

4. A method according to claim 1, wherein the concentration of the tracer fluid is measured a plurality of times as the tracer fluid passes the measuring point.

5. A method according to claim 4, wherein the concentration of the tracer fluid is measured or sampled from when the tracer gas first passes the measuring point until substantially all of the tracer fluid has passed the measuring point.

6. A method according to claim 4, wherein the measured or sampled concentrations of tracer fluid are summed.

7. A method according to claim 4, wherein the measured or sampled concentrations of tracer fluid are integrated with respect to time.

8. A method according to claim 1, wherein the concentration of the tracer fluid is sampled substantially continuously as it passes the measuring point.

9. A method according to claim 8, wherein the concentration of the tracer fluid is measured or sampled from when the tracer gas first passes the measuring point until substantially all of the tracer fluid has passed the measuring point.

10. A method according to claim 8, wherein the measured or sampled concentrations of tracer fluid are summed.

11. A method according to any of claim 8, wherein the measured or sampled concentrations of tracer fluid are integrated with respect to time.

12. A method according to claim 1, wherein the measured or sampled concentrations are adjusted to take account of background tracer fluid concentrations.

13. A method to according to claim 1, wherein the flow rate of the first fluid through the conduit is determined dependent upon the molar quantity of tracer fluid injected into the first fluid.

14. A method to according to claim 1, wherein the flow rate of the first fluid through the conduit is determined dependent upon the concentration of tracer fluid injected into the first fluid.

15. A method to according to claim 1, wherein the tracer fluid includes helium.

16. A method to according to claim 1, wherein the first fluid is a gas.

17. A method according to claim 15, wherein the first fluid is natural gas.

18. A method of measuring the flow rate of a first fluid flowing through a conduit according to claim 1, wherein the flow rate is determined independent of information about the conduit geometry.

19. An apparatus for measuring a flow rate of a first single phase fluid flowing through a conduit, the apparatus comprising a device for discharging a pulse of tracer fluid into a first fluid flowing in a conduit;

determining means for determining a concentration of the tracer fluid at a point downstream from where the discharging device is arranged to discharge the tracer fluid; and control means for determining a flow rate of a first fluid through a conduit dependent upon the known or determinable molar quantity of the tracer fluid discharged and the concentration of the tracer fluid determined by the determining means, wherein the determining means includes a measuring means for measuring a change in thermal conductivity of the mixture of first fluid and tracer fluid compared with a thermal conductivity of the first fluid alone which is dependent upon the concentration of the tracer gas and the determining means includes conversion means for converting the measured change in thermal conductivity into a value corresponding to the tracer fluid concentration.

20. An apparatus according to claim 19, wherein the conversion means converts the measured change in thermal conductivity into a corresponding tracer fluid concentration using suitable algorithms.

21. An apparatus according to claim 20, wherein the measuring means includes a thermal conductivity detector for detecting the thermal conductivity of the passing fluid which is a function of its concentration of tracer fluid.

22. An apparatus according to claim 19, wherein the conversion means converts the measured change in thermal conductivity into a corresponding tracer fluid concentration using a look-up table.

23. Ah apparatus according to claim 19, wherein the tracer fluid is injected into the first fluid.

24. An apparatus according to claim 19, wherein the control means is arranged to receive a plurality of concentration measurements taken as the tracer fluid passes the measuring means.

25. An apparatus according to claim 24, wherein the control means is arranged to receive substantially continuous concentration samples as the tracer fluid passes the measuring means.

26. An apparatus according to claim 25, wherein the control means is arranged to receive concentration measurements or samples from at least when the tracer fluid first passes the measuring point until substantially all of the tracer fluid has passed the measuring point.

27. An apparatus according to claim 25, wherein the control means sums the measured or sampled concentrations of tracer fluid.

28. An apparatus according to claim 25, wherein the control means integrates the measured or sampled concentrations of tracer fluid with respect to time.

29. An apparatus according to claim 25, wherein the control means is arranged to take account of background tracer fluid concentrations in its determination of the flow rate of a first fluid.

30. An apparatus according to claim 24, wherein the control means is arranged to receive concentration measurements or samples from at least when the tracer fluid first passes the measuring point until substantially all of the tracer fluid has passed the measuring point.

31. An apparatus according to claim 24, wherein the control means sums the measured or sampled concentrations of tracer fluid.

32. An apparatus according to claim 24, wherein the control means integrates the measured or sampled concentrations of tracer fluid with respect to time.

33. An apparatus according to claim 24, wherein the control means is arranged to take account of background tracer fluid concentrations in its determination of the flow rate of a first fluid.

34. An apparatus according to claim 24, wherein the control means is arranged to take account of the molar quantity of tracer fluid injected into the first fluid by the discharging device in its determination of the flow rate of a first fluid.

35. An apparatus according to claim 24, wherein the control means is arranged to take account of the concentration of the tracer fluid discharged into the first fluid by the discharging device in its determination of the flow rate of a first fluid.

36. An apparatus according to claim 19, wherein the control means is arranged to take account of the molar quantity of tracer fluid injected into the first fluid by the discharging device in its determination of the flow rate of a first fluid.

37. An apparatus according to claim 19, wherein the control means is arranged to take account of the concentration of the tracer fluid discharged into the first fluid by the discharging device in its determination of the flow rate of a first fluid.

38. An apparatus according to claim 19, wherein the measuring means includes a thermal conductivity detector for detecting the thermal conductivity of the passing fluid which is a function of its concentration of tracer fluid.

39. An apparatus according to claim 19, wherein the flow rate of a fluid through a conduit is determined independent of information about the geometry of the conduit through which the first fluid flows.

40. An apparatus for measuring a flow rate of a first single phase fluid flowing through a conduit, comprising
a discharge device configured to discharge a pulse of tracer fluid into a first fluid flowing in a conduit;
a concentration determination unit configured to determine a concentration of the tracer fluid at a point downstream from where the discharge device is arranged to discharge the tracer fluid; and
a control unit configured to determine a flow rate of a first fluid through the conduit dependent upon the known or determinable molar quantity of the tracer fluid discharged and the concentration of the tracer fluid determined by the concentration determination unit,
wherein the concentration determination unit includes
a thermal conductivity measurement device configured to measure a change in thermal conductivity of a mixture of the first fluid and tracer fluid compared with a thermal conductivity of the first fluid alone which is dependent upon the concentration of the tracer gas, and
a converter configured to convert the measured change in thermal conductivity into a value corresponding to the tracer fluid concentration.

* * * * *